US005304469A

United States Patent [19]

Wilson, III

[11] Patent Number: 5,304,469
[45] Date of Patent: Apr. 19, 1994

[54] PROPYLENE GLYCOL AS AN ACTIVATOR FOR PHOSPHOENOLPYRUVATE CARBOXYLASE

[75] Inventor: Charlie W. Wilson, III, N. Richland Hills, Tex.

[73] Assignee: Abbott Laboratories, Abbott Park, Ill.

[21] Appl. No.: 422,873

[22] Filed: Oct. 17, 1989

[51] Int. Cl.$^5$ .......................... C12Q 1/00; C12Q 1/54; C12Q 1/48; C12Q 1/34
[52] U.S. Cl. ............................. 435/25; 435/4; 435/14; 435/15; 435/18; 435/183
[58] Field of Search ............... 435/25, 4, 14, 15, 18, 435/183; 436/18

[56] References Cited

U.S. PATENT DOCUMENTS

| | | | |
|---|---|---|---|
| 3,963,578 | 6/1976 | Aitken et al. | 435/4 |
| 3,974,037 | 8/1976 | Adams | 435/26 |
| 4,250,254 | 2/1981 | Modrovich | 435/14 |
| 4,704,365 | 11/1987 | Yost | 436/18 |

OTHER PUBLICATIONS

"Reagents for Enzymatic Analysis" in *Methods of Enzymatic Analysis*, 3rd ed. Bergmeyer [Weinheim: Verlag Chemic, 1983].

"Carbon Dioxide and Bicarbonate" in *Manometric & Biochemical Techniques*, ed. Umbreit [Minneapolis: Buress Publishing Co., 1972].

Waygood et al., Can. J. Bot, (1969) 47:1455-58.

*Primary Examiner*—Robert A. Wax
*Assistant Examiner*—Miguel H. Escallon
*Attorney, Agent, or Firm*—Richard D. Schmidt

[57] ABSTRACT

The present invention provides an improved method and reagent for measuring the total carbon dioxide content in a sample of body fluid. The improvement comprises adding a sufficient amount of propylene glycol to the PEPC enzyme reagent to increase the activity of PEPC and maintaining the enzyme reagent at a substantially constant pH of about 6.0 to 7.0.

22 Claims, 1 Drawing Sheet

PROPYLENE GLYCOL AS AN ACTIVATOR FOR PHOSPHOENOLPYRUVATE CARBOXYLASE

BACKGROUND OF THE INVENTION

1. Field of the Invention

The present invention relates to the activation and stabilization of reagents used in enzymatic assays. In particular, the invention relates to the use of propylene glycol, at suitable pH levels, to increase the specific activity of the phosphoenolpyruvate carboxylase (PEPC) enzyme reagent used in carbon dioxide assays.

2. Description of Related Art

The total carbon dioxide content of serum consists primarily of bicarbonate ions ($HCO_3^-$) which account for 90 to 95 percent of the total carbon dioxide ($CO_2$) content, and the remaining serum $CO_2$ is present in the physically dissolved state. Bicarbonate has a normal serum level range of 23 to 32 meq/L and is the second largest fraction of anions present in serum. Clinically, an alteration of the serum bicarbonate level is reflective of an acid-base imbalance. An analysis of the bicarbonate concentration, together with an evaluation of electrolytes and other blood gases, will give an overall picture of the acid-base imbalance.

A typical carbon dioxide assay utilizes PEPC and an enzymatic reaction to determine the total carbon dioxide concentration. ("Reagents for Enzymatic Analysis," in *Methods of Enzymatic Analysis*, 3d ed. Bergmeyer [Weinheim: Verlag Chemie, 1983], 275-76.) The assay can be depicted by the following reactions:

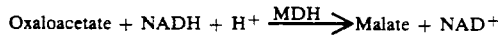

wherein $P_i$ is inorganic phosphorus, NADH is the reduced form of nicotinamide adenine dinucleotide, MDH is malate dehydrogenase and $NAD^+$ is the oxidized form of nicotinamide adenine dinucleotide. The two step reaction can be monitored by measuring the disappearance of NADH at the bichromatic wavelength of 340/380 nanometers (nm), i.e., the decrease in NADH concentration is proportional to the amount of carbon dioxide in the sample. Alternatively, the first enzyme reaction can be monitored by measuring either the quantity of oxaloacetate produced or the rate at which the oxaloacetate is produced.

Reagent stability is a critical problem with assay reagents utilized to determine total carbon dioxide concentration. Conventional PEPC enzyme reagent formulations are stable for only about four to eight hours. Carbon dioxide in solution is in a state of equilibrium between dissolved carbon dioxide and carbonic acid which dissociates to form $H^+$ and $HCO_3^-$ in accordance with the following equation:

("Carbon Dioxide and Bicarbonate," in *Manometric & Biochemical Techniques*, ed. Umbreit [Minneapolis: Burgess Publishing Co., 1972], 20. The reagents are destabilized by the absorption of carbon dioxide from the atmosphere; the $CO_2$ enters the reaction sequence and consumes the phosphoenolpyruvate and NADH present in the reagent. Conventional assays are based upon the principle that a pH of about 7.5 to about 10.5 is necessary for the conversion of both dissolved $CO_2$ and carbonic acid to the bicarbonate ion, as disclosed by Adams in U.S. Pat. No. 3,974,037. It is now believed that the actual substrate of the PEPC enzyme is $CO_2$. (Waygood et al., *Can. J. Bot.* (1969) 47: 1455-58.)

There is a need, therefore, for a PEPC enzyme reagent which is stable in the atmosphere under normal conditions of use and which has a pH level suitable for use in an assay designed to measure bicarbonate as a function of $CO_2$ concentration.

SUMMARY OF THE INVENTION

The present invention involves an improved method and reagent for measuring the total carbon dioxide content in a sample of body fluid. In the assay method, phosphoenolpyruvate and PEPC enzyme reagent are added to a test sample to provide a reaction mixture. The phosphoenolpyruvate reacts with carbon dioxide contained in the sample in the presence of PEPC to produce oxaloacetate, and the quantity of or the rate at which oxaloacetate is formed is then measured. The improvement comprises adding a sufficient amount of a polyhydroxyl alkyl solvent such as propylene glycol, or methanol, to the PEPC enzyme reagent to increase the activity of PEPC and maintaining the enzyme reagent at a substantially constant pH of about 6.0 to about 7.0. Preferably, the enzyme reagent solution has a pH of about 6.3 to about 7.0, and still more preferably of about 6.5 to about 7.0. The amount of propylene glycol present in the enzyme reagent is about 0.1% to about 50%. Preferably, the amount of propylene glycol present in the enzyme reagent is about 5% to about 40%, and still more preferably, the amount of propylene glycol present in the enzyme reagent is about 20%.

In an alternative method for measuring the total carbon dioxide content of a test sample, malate dehydrogenase and the reduced form of nicotinamide adenine dinucleotide are also included in the enzyme reagent solution. The phosphoenolpyruvate reacts with carbon dioxide contained in the test sample in the presence of PEPC to produce oxaloacetate, and the oxaloacetate and NADH in the presence of malate dehydrogenase react to produce malate and $NAD^+$. The assay is monitored by determining the change in the concentration of the NADH in the reaction mixture. The improvement again involves including an amount of a polyhydroxyl alkyl solvent such as propylene glycol, or methanol, sufficient to increase the activity of the PEPC while maintaining a substantially constant pH of about 6.0 to about 7.0 for the enzyme reagent solution.

The improved enzyme reagent solution of the present invention contains PEPC and propylene glycol, wherein the propylene glycol is present in an amount sufficient to enhance the activity of PEPC, and wherein the pH of the reagent is about 6.0 to about 7.0. The solution can be made by combining the propylene glycol with a solution of phosphoenolpyruvate and PEPC. Alternatively, the enzyme reagent solution can be made by reconstituting a lyophilized enzyme reagent containing phosphoenolpyruvate, PEPC and a bulking agent with a diluent comprising propylene glycol, wherein the propylene glycol is present in an amount sufficient to increase the activity of PEPC, and wherein the pH of the enzyme reagent solution is about 6.0 to about 7.0.

DETAILED DESCRIPTION OF THE INVENTION

Figure 1:
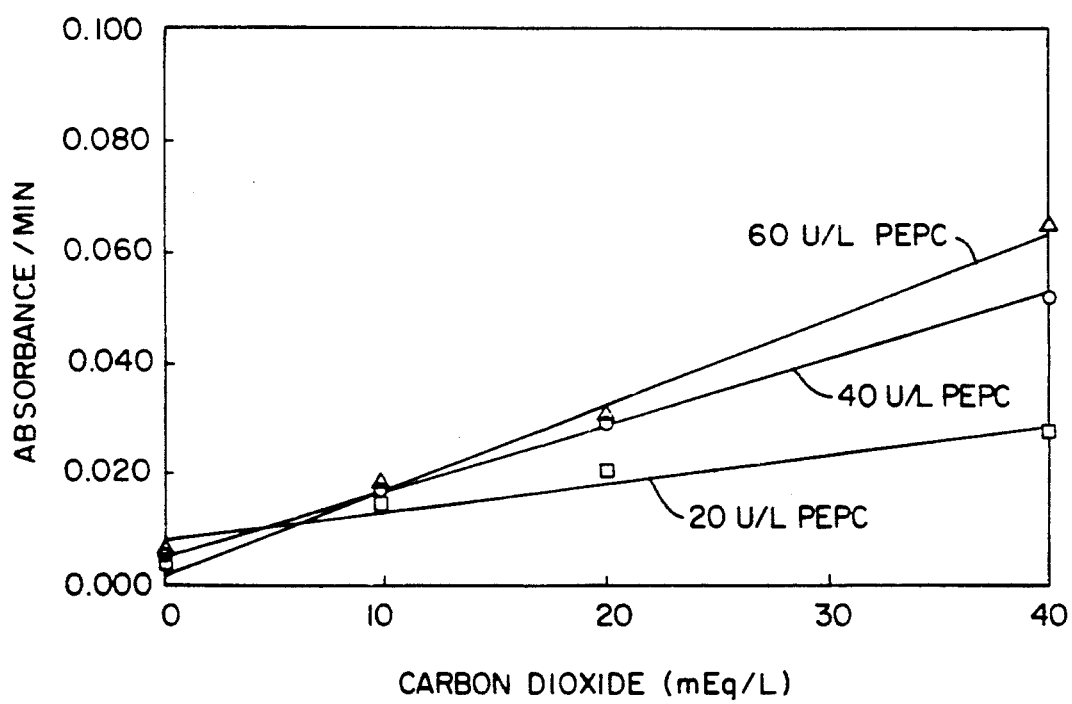
FIG. 1 shows the total carbon dioxide concentration versus the change in absorbance for enzyme reagents of the present invention containing 20% propylene glycol and PEPC concentrations of 20, 40 and 60 U/L, respectively.

The present invention involves the activation of the phosphoenolpyruvate carboxylase (PEPC) enzyme, used in carbon dioxide assays, by the addition of a polyhydroxyl alkyl solvent such as propylene glycol, or methanol. It has been discovered that the addition of propylene glycol to PEPC will increase the specific activity of PEPC. The use of propylene glycol in the enzyme reagent is especially advantageous because the "activated" PEPC can be used in decreased amounts due to its enhanced activity in the presence of propylene glycol.

It has also been found that it is especially advantageous to maintain the pH of the enzyme reagent at a substantially constant level of about 6.0 to about 7.0. The benefits are three-fold. First, PEPC is activated by propylene glycol only at the pH range of about 6.0 to about 7.0. Secondly, the reagent is more stable because $CO_2$ flux from the atmosphere into the reagent solution is reduced when the solution has a pH between about 6.0 to about 7.0. For example, an enzyme reagent of the present invention containing propylene glycol at a pH of about 6.5 has a stability of from about 24 to about 30 hours. This is a 3- to 7-fold increase in stability in comparison to the 4 to 8 hour stability of the reagents of the prior art which do not contain propylene glycol and which maintain a pH of about 7.5 to about 10.5 to promote the conversion of $CO_2$ to $HCO_3^-$. Thirdly, the reagents of the present invention, maintained at the pH range of about 6.0 to about 7.0, shift the equilibrium between dissolved $CO_2$, carbonic acid and bicarbonate towards $CO_2$. Because $CO_2$ is the probable substrate for the enzyme, a pH that promotes the conversion of $HCO_3^-$ to $CO_2$ is desired. Therefore, in the present invention, the enzyme reagent solution is maintained at a substantially constant pH of about 6.0 to about 7.0, more preferably of about 6.3 to about 7.0, and still more preferably of about 6.5 to about 7.0.

The concentration range of propylene glycol in the enzyme reagent will be about 0.1% to about 50%, and more preferably will be about 5% to about 40%. An especially preferred enzyme reagent is one in which the propylene glycol is added at a final concentration in the enzyme reagent of about 20%. Optionally, the propylene glycol can be treated to remove peroxides and aldehydes, but this is not essential to the practice of the present invention.

An "enzyme reagent," in accordance with the present invention, can be a solution or a lyophilized powder reagent. The enzyme reagent solution can be made by combining the propylene glycol with a solution of phosphoenolpyruvate and PEPC. Alternatively, MDH and NADH can also be added to the solution containing phosphoenolpyruvate and PEPC. An enzyme reagent that is in the form of a lyophilized powder can be converted to form the reagent solution merely by adding an appropriate diluent. The "lyophilized powder reagent" contains enzymes and substrates utilized in the reaction, which are each lyophilized separately and then blended with buffers and inert bulking agents, such as lactose, bovine serum albumin, mannose and the like, the use of which are well known in the art. While a preferred buffer is PIPES (piperazine-N,N'-bis[2-ethanesulfonic acid]), other buffers such as HEPES (N-[2-hydroxyethyl]piperazine-N'-[2-ethanesulfonic acid], MES (2-[N-morpholino]ethanesulfonic acid), BIS-TRIS (bis[2-hydroxyethyl]iminotris[hydroxymethyl]methane), ADA (N-[2-acetamido]-2-iminodiacetic acid), ACES (2-[(2-amino-2-oxoethyl)amino]ethanesulfonic acid), MOPSO (3-[N-morpholino]-2-hydroxypropanesulfonic acid), BES (N,N-bis[2-hydroxyethyl]-2-aminoethanesulfonic acid), MOPS (3-[N-morpholino]propanesulfonic acid), and TES (N-tris[hydroxymethyl]methyl-2-aminoethanesulfonic acid) may be employed, as understood in the art. For example, the lyophilized powder reagent can comprise phosphoenolpyruvate, lyophilized PEPC, lyophilized MDH and lyophilized NADH, magnesium acetate, PIPES and a lactose bulking agent. In addition, oxalate can be added to the reagent to inhibit the activity of lactate dehydrogenase (LDH) which is often contained in human body fluids. The addition of oxalate prevents the LDH reaction from competing with and thereby interfering with the determination of total carbon dioxide. (See U.S. Pat. No. 3,956,069.) The diluent for the lyophilized powder reagent contains an amount of propylene glycol sufficient to enhance the activity of the PEPC and an appropriate aqueous solution of buffer(s) and/or salt(s). While a preferred buffer for the diluent is acetate, other buffers such as citrate, MES, BIS-TRIS and ADA may be employed, as understood in the art. Suitable salts which may be employed include NaCl and KCl, also as understood in the art. The pH range of the diluent will be from about 2.0 to about 6.2, more preferably from about 4.0 to about 6.2, and still more preferably from about 5.8 to about 6.2. An especially preferred diluent is one in which the pH is about 6.0.

Enzyme reagent solutions of the present invention can be utilized in enzyme assays to determine total carbon dioxide content. For example, a endpoint reaction comprises non-limiting quantities of substrates (e.g., PEP) and enzymes (e.g., PEPC and MDH), such that all of the carbon dioxide from the test sample is utilized in the reaction. Alternatively, a rate reaction comprises rate-limiting quantities of enzymes (e.g., PEPC and MDH), such that the rate of carbon dioxide utilization is regulated by its concentration.

Body fluids which are easily tested by the method of the present invention include whole blood, plasma, serum, cerebrospinal fluid and the like.

EXAMPLES

The preparation of the novel enzyme reagents and their utilization in carbon dioxide assays of the present invention are illustrated in more detail in the following examples.

EXAMPLE 1

The following experiment was performed to investigate the effects of varying the concentrations of NADH, phosphoenolpyruvate (PEP) and propylene glycol, on the reaction rate of the PEPC reagent.

A standard PEPC enzyme reagent was prepared comprising 100 mM HEPES (N-[2-hydroxyethyl]piperazine-N'-[2-ethanesulfonic acid], pH 7.0; Sigma Chemical Co., St. Louis, Mo.), 0.44 mM NADH (Boehringer-Mannheim, Indianapolis, Ind.), 5.0 mM PEP (JBL Scientific, Inc., San Luis Obispo, Calif.), 6.7 mM $MgCl_2 \cdot 6H_2O$, 5000 U/L MDH (Calzyme Laboratories, Inc., San Luis Obispo, Calif.), and 200 U/L PEPC (Diagnostic Chemicals, Ltd., Monroe, Conn.). The standard reagent did not contain propylene glycol. The concentrations of NADH, PEP, and propylene glycol were increased, one at a time, to 0.9 mM, 6.5 mM and 5%, respectively. The propylene glycol, which was added to the standard reagent to form a reagent solution of the present invention, was treated to remove peroxides and aldehydes.

Bicarbonate standards of 0, 10, 20 and 40 meq/L (New England Reagent Laboratory, East Providence, R.I.) were added to the above-prepared enzyme reagent solutions, and the reaction mixtures so formed were assayed at 37° C. for initial reaction rate of PEPC. The assays were performed on the Abbott Spectrum ® Instrument, commercially available from Abbott Laboratories, North Chicago, Ill., according to manufacturer's instructions. The reaction was monitored at the bichromatic wavelength pair 340/404 nm, except for the assay of the reagent containing the increased NADH concentration which was monitored at 364/404 nm. The enzyme reagent solution of the present invention containing 5% propylene glycol showed an accelerated reaction rate in comparison to the standard PEPC reagent which did not contain propylene glycol.

EXAMPLE 2

The following experiment was performed to study the effects of various propylene glycol concentrations on the activation of PEPC.

A standard enzyme reagent was prepared comprising 100 mM PIPES (piperazine-N,N'-bis[2-ethanesulfonic acid]; Sigma Chemical Co.), 0.44 mM NADH, 5.0 mM PEP, 6.7 mM $MgCl_2 \cdot 6H_2O$, 20,000 U/L MDH and 10 mM $K_2CO_3$. Propylene glycol was then added to the standard reagent, in varying concentrations of 0, 1, 2, 5, 10 and 20% to produce the novel enzyme reagents of the present invention. The propylene glycol had been treated to remove peroxides and aldehydes. All reagent solution volumes were equalized by adding water. After mixing, the solutions were adjusted to pH 6.5.

PEPC samples, having concentrations of 0, 200, 500 and 1000 U/L, were added to the above-prepared solutions which were previously heated to 37° C., and the reaction mixtures so formed were assayed at 37° C. for PEPC activity on the Abbott Spectrum ® Instrument, substantially in accordance with the procedure of Example 1. The results from a representative assay of the test sample having a PEPC concentration of 200 U/L are presented in Table 1. The results show that increasing the concentration of propylene glycol in the enzyme reagents of the present invention had the effect of increasing the PEPC enzyme activity.

TABLE 1

| Enzyme Activity of Sample Containing 200 U/L PEPC | |
|---|---|
| Propylene glycol concentration (%) | PEPC Activity (U/L) |
| 0 | 6 |
| 1 | 39 |
| 2 | 65 |
| 5 | 76 |
| 10 | 148 |
| 20 | 200 |

EXAMPLE 3

Using a standard reagent prepared substantially in accordance with that described in Example 2, a variety of enzyme reagent solutions were prepared to test the activation of PEPC at higher propylene glycol concentrations.

Propylene glycol, that had been treated to remove peroxides and aldehydes, was added to the standard reagent in concentrations of 0, 10, 20, 40 and 60% to prepare the novel enzyme reagents of the present invention. In addition, a 20% untreated propylene glycol solution was prepared. All solution final volumes were made equal by adding water. After mixing, the pH was adjusted to 6.5.

Samples of PEPC, having concentrations of 0, 200, 500 and 1000 U/L, were added to the above-prepared solutions and assayed for PEPC activity on the Abbott Spectrum ® Instrument, substantially in accordance with the procedure of Example 1. The results from a representative assay of the sample having a PEPC concentration of 200 U/L are illustrated in Table 2. The results show that the optimal concentration of propylene glycol is approximately 20% in the enzyme reagents of the present invention. The reagent solution containing untreated propylene glycol produced substantially similar results.

TABLE 2

| Enzyme Activity of Sample Containing 200 U/L PEPC | |
|---|---|
| Propylene glycol concentration (%) | PEPC Activity (U/L) |
| 0 | 150 |
| 10 | 440 |
| 20 | 510 |
| 40 | 215 |
| 60 | 18 |

EXAMPLE 4

The following experiment was performed to determine the optimum concentration of PEPC in a 20% propylene glycol enzyme reagent solution of the present invention.

In addition to having a 20% propylene glycol concentration, the reagent solution comprised 100 mM PIPES (pH 6.5), 0.9 mM NADH, 5.0 mM PEP, 6.7 mM $MgCl_2 \cdot 6H_2O$ and 5000 U/L MDH. The pH of the solution was adjusted to 6.5. Varying amounts of a 0.72 U/mg lyophilized PEPC were added to provide enzyme reagents having final concentrations of 10, 20, 40, 60, 80, and 100 U/L PEPC.

Bicarboante standards of 0, 10, 20 and 40 meq/L (New England Reagent Laboratory) were added to the above-prepared solutions and assayed for the initial reaction rate of PEPC on the Abbott Spectrum ® Instrument, substantially in accordance with the procedure of Example 1. Total carbon dioxide concentrations ($CO_2$) were plotted versus the change in absorbance for the different PEPC concentrations. As illustrated in FIG. 1, the results showed that the PEPC initial reaction rate is linear in the range from about 40 U/L to about 60 U/L PEPC.

EXAMPLE 5

The following experiment was performed to study the effect of pH on the activation of PEPC.

A standard enzyme reagent was prepared comprising 50 mM PIPES, 0.14 mM NADH, 10.0 mM PEP, 6.7 mM MgCl$_2$.6H$_2$O, 5000 U/L MDH, 10 mM NaHCO$_3$ and 500 U/L PEPC. Propylene glycol was added in varying concentrations of 0, 5, 10, and 20% to provide novel enzyme reagent solutions in accordance with the present invention. The pH of each enzyme reagent was varied from 6.3 to 8.0. The assays were performed on the Abbott Spectrum® Instrument, substantially in accordance with the procedure of Example 1.

As summarized in Table 3, the enzyme reagent solutions containing propylene glycol had increased activity when the pH of the reagent ranged from about 6.0 to about 7.0 as compared to the standard reagent which did not contain propylene glycol (i.e., 0% propylene glycol).

TABLE 3

Propylene Glycol Activation of PEPC as a Function of pH

| Propylene glycol concentration (%) | PEPC Activity (U/L) | | | | |
|---|---|---|---|---|---|
| | pH 6.3 | pH 6.6 | pH 7.0 | pH 7.5 | pH 8.0 |
| 0 | 126 | 465 | 1139 | 1175 | 999 |
| 5 | 275 | 733 | 1181 | 1108 | 968 |
| 10 | 453 | 868 | 1108 | 1042 | 870 |
| 20 | 561 | 710 | 846 | 782 | 738 |

EXAMPLE 6

The following experiment was performed to study the effect of pH on the activation of PEPC, utilizing methanol as an activator. The experiment was run according to the methods disclosed in Example 5, with the following exceptions. The enzyme reagent contained 100 mM HEPES, and methanol was added in varying concentrations of 0, 1, 5, 10 and 20% to provide novel enzyme reagent solutions in accordance with the present invention. Each enzyme reagent was tested at a pH of 6.5 and 8.0.

As summarized in Table 4, the enzyme reagent solutions containing methanol had increased activity when the pH ranged from about 6.0 to about 7.0 as compared to the reagent which did not contain methanol (i.e., 0% methanol).

TABLE 4

Methanol Activation of PEPC as a Function of pH

| Methanol concentration (%) | PEPC Activity (U/L) | |
|---|---|---|
| | pH 6.5 | pH 8.0 |
| 0 | 100 | 1436 |
| 1 | 211 | 1538 |
| 5 | 329 | 1726 |
| 10 | 607 | 1788 |
| 20 | 540 | 1132 |

It will be appreciated by one skilled in the art that the embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

I claim:

1. In a method for measuring the total carbon dioxide content of a test sample, comprising the steps of:
    adding a reagent solution of phosphoenolpyruvate and phosphoenolpyruvate carboxylase (PEPC) to the sample to form a reaction mixture, wherein said phosphoenolpyruvate reacts with carbon dioxide contained in the sample to produce oxaloacetate; and
    measuring the quantity of or the rate at which oxaloacetate is formed in said mixture;
    the improvement comprising adding to said reagent solution an amount of a solvent sufficient to increase the activity of said PEPC while maintaining a pH of about 6.0 to about 7.0, wherein said solvent is propylene glycol.

2. The method according to claim 1 wherein the pH is maintained at about 6.5 to about 7.0.

3. The method according to claim 1 wherein said propylene glycol is treated to remove peroxides and aldehydes.

4. The method according to claim 1 wherein said propylene glycol is added at a final concentration of from about 0.1% to about 50%.

5. The method according to claim 4 wherein said propylene glycol is added at a final concentration of about 20%.

6. In a method for measuring the total carbon dioxide content of a test sample, comprising the steps of:
    adding a reagent solution of phosphoenolpyruvate, phosphoenolpyruvate carboxylase (PEPC), malate dehydrogenase and the reduced form of nicotinamide adenine dinucleotide (NADH) to the sample to form a reaction mixture, wherein said phosphoenolpyruvate reacts with carbon dioxide contained in the sample to produce oxaloacetate, and wherein said malate dehydrogenase, NADH and oxaloacetate react; and
    determining the change in the concentration of said NADH in said mixture;
    the improvement comprising adding to said reagent solution an amount of a solvent sufficient to increase the activity of said PEPC while maintaining a pH of about 6.0 to about 7.0, wherein said solvent is propylene glycol.

7. The method according to claim 6 wherein the pH is maintained at about 6.5 to about 7.0.

8. The method according to claim 7 wherein said propylene glycol is treated to remove peroxides and aldehydes.

9. The method according to claim 7 wherein said propylene glycol is added at a final concentration of about 0.1% to about 50%.

10. The method of claim 9 wherein said propylene glycol is added at a final concentration of about 20%.

11. An enzyme reagent solution, comprising: phosphoenolpyruvate carboxylase (PEPC) and a solvent, wherein said solvent is present in an amount sufficient to increase the activity of PEPC and said solvent is propylene glycol and wherein the pH of the reagent is about 6.0 to about 7.0.

12. The reagent according to claim 11 wherein said propylene glycol is treated to remove peroxides and aldehydes.

13. The reagent according to claim 11 wherein said propylene glycol is present at a final concentration of about 0.1% to about 50%.

14. The reagent according to claim 13 wherein said propylene glycol is present at a final concentration of about 20%.

15. An enzyme reagent solution made by a process comprising the steps of:
    reconstituting a lyophilized enzyme reagent comprising phosphoenolpyruvate, phosphoenolpyruvate carboxylase (PEPC) and a bulking agent with a diluent comprising a solvent, wherein said solvent is present in an amount sufficient to increase the activity of PEPC and said solvent is selected from the group consisting of propylene glycol and methanol, and wherein the pH of the reagent is about 6.0 to about 7.0.

16. The reagent according to claim 15 wherein said propylene glycol is treated to remove peroxides and aldehydes.

17. The reagent according to claim 15 wherein said propylene glycol is present at a final concentration of about 0.1% to about 50%.

18. The reagent according to claim 17 wherein said propylene glycol is present at a final concentration of about 20%.

19. The reagent according to claim 15 wherein said bulking agent is selected from the group consisting of lactose, bovine serum albumin and mannose.

20. The reagent according to claim 15 further comprising oxalate to inhibit the activity of lactate dehydrogenase.

21. The reagent according to claim 15 further comprising malate dehydrogenase and the reduced form of nicotinamide adenine dinucleotide.

22. The reagent according to claim 15 wherein said diluent has a pH of about 5.8 to about 6.2.

* * * * *